US009084726B2

(12) United States Patent
Egberg et al.

(10) Patent No.: US 9,084,726 B2

(45) Date of Patent: Jul. 21, 2015

(54) SUSPENSION COMPOSITIONS OF PHYSIOLOGICALLY ACTIVE PHENOLIC COMPOUNDS AND METHODS OF MAKING AND USING THE SAME

(71) Applicant: Humanetics Corporation, Eden Prairie, MN (US)

(72) Inventors: David C. Egberg, Bonita Springs, FL (US); Michael D. Kaytor, Maplewood, MN (US); John C. Dykstra, Eden Prairie, MN (US)

(73) Assignee: Humanetics Corporation, Minneapolis, MN (US)

( * ) Notice: Subject to any disclaimer, the term of this patent is extended or adjusted under 35 U.S.C. 154(b) by 0 days.

(21) Appl. No.: 14/090,864

(22) Filed: Nov. 26, 2013

(65) Prior Publication Data

US 2015/0147359 A1 May 28, 2015

(51) Int. Cl.
*A61K 9/10* (2006.01)
*A61K 31/352* (2006.01)

(52) U.S. Cl.
CPC ................. *A61K 9/10* (2013.01); *A61K 31/352* (2013.01)

(58) Field of Classification Search
None
See application file for complete search history.

(56) References Cited

U.S. PATENT DOCUMENTS 4,390,559 A * 6/1983 Zilliken ........................ 426/545
5,302,401 A 4/1994 Liversidge et al.
6,855,359 B2 2/2005 Khare
7,655,694 B2 2/2010 Landauer et al.
8,551,530 B2 10/2013 Elder, Jr. et al.
8,900,635 B2 12/2014 Elder et al.
2004/0164194 A1 8/2004 Reed et al.
2004/0220116 A1* 11/2004 Behnam .......................... 514/27
2006/0116510 A1 6/2006 Behnam
2006/0292214 A1* 12/2006 Jenkins et al. ................ 424/451
2007/0020197 A1 1/2007 Galli et al.
2007/0043121 A1 2/2007 Brown et al.
2007/0087104 A1* 4/2007 Chanamai ..................... 426/602
2007/0269526 A1 11/2007 Bos et al.
2008/0311209 A1 12/2008 Beumer et al.
2009/0035336 A1* 2/2009 Vollhardt et al. ............. 424/401
2009/0035366 A1* 2/2009 Liversidge et al. ........... 424/451
2012/0121654 A1 5/2012 Elder, Jr. et al.
2012/0164190 A1 6/2012 Elder et al.

FOREIGN PATENT DOCUMENTS

WO WO 2012/068140 5/2012

OTHER PUBLICATIONS

Atkinson, et al., "The effects of phytoestrogen isoflavones on bone density in women: a double-blind, randomized, placebo-controlled trial[1-3]", Am. J. Clin. Nutr., vol. 79, pp. 326-333, (2004).

(Continued)

*Primary Examiner* — Robert A Wax
*Assistant Examiner* — Melissa Mercier
(74) *Attorney, Agent, or Firm* — Stoel Rives, LLP; Zhi-Xiang (Alex) Oh

(57) ABSTRACT

The present invention is directed to compositions comprising physiologically active phenolic compounds and methods for making and using the same. In particular embodiments, the compositions described herein include suspension formulations including a physiologically active phenolic compound provided as a nanoparticulate material and dispersed within an edible lipid.

30 Claims, 4 Drawing Sheets

Genivida (before milling)

| | |
|---|---|
| Mean Size | : 35.79615(μm) |
| Median Size | : 29.54557(μm) |
| Mode Size | : 27.8086(μm) |
| S.P. Area | : 2199.7(cm²/cm³) |
| Std.Dev. | : 22.1223(μm) |
| Span | : OFF |
| Diameter on Cumulative % | : (1)10.00(%)- 17.1811(μm) |
| | : (2)50.00(%)- 29.5456(μm) |
| | : (3)90.00(%)- 62.1013(μm) |
| | : (4)97.00(%)- 92.6729(μm) |
| | : (5)99.00(%)- 124.3863(μm) |
| | : (6)99.90(%)- 181.0281(μm) |

q(%) 0 2 4 6 8 10 12 13
UnderSize (%) 0 10 20 30 40 50 60 70 80 90 100
Diameter(μm) 0.010 0.100 1.000 10.00 100.0 1000 3000

(56) References Cited

OTHER PUBLICATIONS

Bhathena, et al., "Beneficial role of dietary phytoestrogens in obesity and diabetes[1,2]," Am. J. Clin. Nutr., vol. 76, pp. 1191-1201, (2002).
Chait, A., "Low-Density Lipoprotein Oxidation and the Pathogenesis of Atherosclerosis," WJM, vol. 160, No. 2, pp. 183-184, Feb. 1994.
Clifton-Bligh, et al., "The effect of isoflavones extracted from red clover (Rimostil) on lipid and bone metabolism," Menopause: The Journal of The North American Menopause Society, vol. 8, No. 4, pp. 259-265, (2001).
Cotter, et al., "Genistein Appears to Prevent Early Postmenopausal Bone Loss as Effectively as Hormone Replacement Therapy," Nutrtion Reviews, vol. 61, No. 10, pp. 346-351, (2003).
Fitzpatrick, L.A., "Soy isoflavones: hope or hype?," Maturitas, vol. 44, Suppl. 1, pp. S21-S29, (2003).
Goodman-Gruen, et al., "Usual dietary isoflavone intake and body composition in postmenopausal women," Menopause: The Journal of the North American Menopause Society, vol. 10, No. 5, pp. 427-432, (2003).
Landauer, et al., "Radioprotective and Locomotor Responses of Mice Treated with Nimodipine Alone and in Combination with WR-151327," Journal of Applied Toxicology, vol. 21, pp. 25-31, (2001).
Landauer, et al., "Genistein Treatment Protects Mice from Ionizing Radiation Injury," Journal of Applied Toxicology, vol. 23, pp. 379-385, (2003).
Landauer, et al., "Prevention of Gamma Radiation-Induced Mortality in Mice by the Isoflavone Genistein," NATO RTG-099, pp. 17-1-17-11, (2005).
Leonarduzzi, et al., "Design and Development of Nanovehicle-Based Delivery Systems for Preventive or Therapeutic Supplementation with Flavonoids," Current Medicinal Chemistry, vol. 17, pp. 74-95, (2010).
Magee, et al., "Phyto-oestrogens, their mechanism of action: current evidence for a role in breast and prostate cancer," British Journal of Nutrition, vol. 91, pp. 513-531, (2004).
Messina, M.J., "Emerging Evidence on the Role of Soy in Reducing Prostate Cancer Risk." Nutrition Reviews, vol. 61, No. 4, pp. 117-131, (Apr. 2003).
Mohammad, et al., "Genistein sensitizes diffuse large cell lymphoma to CHOP (cyclophosphamide, doxorubicin, vincristine, prednisone) chemotherapy," Molecular Cancer Therapeutics, vol. 2, No. 12, pp. 1361-1368, (2003).
Morabito, et al., "Effects of Genistein and Hormone-Replacement Therapy on Bone Loss in Early Postmenopausal Women: A Randomized Double-Blind Placebo-Controlled Study," Journal of Bone and Mineral Research, vol. 17, No. 10, pp. 1904-1912, (2002).
Nicosia, et al., "Oncogenic pathways implicated in ovarian epithelial cancer," Hematology/Oncology Clinics of North America, vol. 17, pp. 927-943, (2003).
Park, et al., "Chemopreventive potential of epigallocatechin gallate and genistein: evidence from epidemiological and laboratory studies," Toxicology Letters, vol. 150, pp. 43-56, (2004).
Roomans, G.M., "Pharmacological Approaches to Correcting the Ion Transport Defect in Cystic Fibrosis," Am. J. of Respir. Med., vol. 2, No. 5, pp. 413-431, (2003).
Sarkar, et al., "Soy Isoflavones and Cancer Prevention," Cancer Investigation, vol. 21, No. 5, pp. 744-757, (2003).
Sarkar, et al., "Lesson Learned from Nature for the Development of Novel Anti-Cancer Agents: Implication of Isoflavone, Curcumin, and their Synthetic Analogs," Curr. Pharm. Des., vol. 16, No. 16, pp. 1801-1812, (Jun. 2010).
Setchell, et al., "Dietary phytoestrogens and their effect on bone: evidence from in vitro and in vivo, human observational, and dietary intervention studies[1-3]," Am. J. Clin. Nutr., vol. 78(suppl.), pp. 593S-609S, (2003).
Si, et al., "Improving the Anti-Tumor Effect of Genistein with a Biocompatible Superparamagnetic Drug Delivery System," Journal of Nanoscience and Nanotechnology, vol. 10, No. 4, pp. 2325-2331, (2010).
Sun, et al., "Pilot Study of a Specific Dietary Supplement in Tumor-Bearing Mice and in Stage IIIB and IV Non-Small Cell Lung Cancer Patients," Nutrition and Cancer, vol. 39, No. 1, pp. 85-95, (2001).
Takimoto, et al., "Phase I Pharmacokinetic and Pharmacodynamic Analysis of Unconjugated Soy Isoflavones Administered to Individuals with Cancer," Cancer Epidemiology, Biomarkers & Prevention, vol. 12, pp. 1213-1221, (Nov. 2003).
Urban, et al., "The Effect of Isolated Soy Protein on Plasma Biomarkers in Elderly Men with Elevated Serum Prostate Specific Antigen," The Journal Urology, vol. 165, pp. 294-300, (Jan. 2001).
Wei, et al., "Isoflavone Genistein: Photoprotection and Clinical Implications in Dermatology[1,2]," The Journal of Nutrition, vol. 133, pp. 3811S-3819S, (2003).
Zhou, et al., "Genistein Stimulates Hematopoiesis and Increases Survival in Irradiated Mice," J. Radiat. Res., vol. 46, pp. 425-433, (2005).
Office Action issued Mar. 21, 2012 in U.S. Appl. No. 12/946,711.
Response to the Mar. 21, 2012 Office Action filed Jun. 21, 2012, in U.S. Appl. No. 12/946,711.
Office Action issued Aug. 31, 2012 in U.S. Appl. No. 12/946,711.
Response to the Aug. 31, 2012 Office Action filed Feb. 14, 2013, in U.S. Appl. No. 12/946,711.
Final Rejection issued Oct. 8, 2013, in U.S. Appl. No. 12/946,711.
Office Action issued Mar. 28, 2012 in U.S. Appl. No. 13/411,405.
Response to the Mar. 28, 2012 Office Action filed Jun. 27, 2012, in U.S. Appl. No. 13/411,405.
Office Action issued Sep. 11, 2012 in U.S. Appl. No. 13/411,405.
Response to the Sep. 11, 2012 Office Action filed Dec. 11, 2012, in U.S. Appl. No. 13/411,405.
Third Office Action issued Feb. 22, 2013, in U.S. Appl. No. 13/411,405.
International Search Report and Written Opinion issued Mar. 23, 2012, in International Application No. PCT/US2011/060829.
International Preliminary Report on Patentability issued May 21, 2013, in International Application No. PCT/US2011/060829.
Young, et al., "Why are Low-Density Lipoproteins Atherogenic," WJM, vol. 160, No. 2, pp. 153-164, Feb. 1994.
Applicant Initiated Interview Summary issued Dec. 14, 2012 in U.S. Appl. No. 12/946,711.
Office Action issued Oct. 8, 2013 in U.S. Appl. No. 12/946,711.
Response to the Oct. 8, 2013 Office Action filed Mar. 7, 2014 in U.S. Appl. No. 12/946,711.
Applicant Initiated Interview Summary issued Dec. 14, 2012 in U.S. Appl. No. 13/411,405.
Response to the Feb. 22, 2013 Office Action filed May 22, 2013 in U.S. Appl. No. 13/411,405.
Applicant Initiated Interview Summary issued May 29, 2013 in U.S. Appl. No. 13/411,405.
Notice of Allowance issued Jun. 24, 2013 in U.S. Appl. No. 13/411,405.
Notice of Allowance issued Jul. 30, 2014 in U.S. Appl. No. 12/946,711.
Notice of Allowance issued Sep. 9, 2014 in U.S. Appl. No. 12/946,711.
Notice of Allowance issued Sep. 18, 2014 in U.S. Appl. No. 12/946,711.
International Search Report and Written Opinion issued Feb. 6, 2015 in International Application No. PCT/US14/67141.
Preliminary Amendment filed Oct. 27, 2014 in U.S. Appl. No. 14/524,936.

* cited by examiner

<table>
<tr><th>Particle Size Data:</th><th>Initial Measurement</th><th>3-Month Measurement</th></tr>
<tr><td>Bonistein</td><td>Mean Size : 0.47825(μm)<br>Median Size : 0.25334(μm)<br>Mode Size : 0.2412(μm)<br>S.P. Area : 2.5236E+5(cm²/cm³)<br>Std.Dev. : 0.6221(μm)<br>Span : OFF<br>Diameter on Cumulative % : (1)10.00(%)- 0.1348(μm)<br>: (2)50.00(%)- 0.2533(μm)<br>: (3)90.00(%)- 1.3022(μm)<br>: (4)97.00(%)- 2.3668(μm)<br>: (5)99.00(%)- 3.1048(μm)<br>: (6)99.90(%)- 4.1686(μm)</td><td>Mean Size : 0.60847(μm)<br>Median Size : 0.28305(μm)<br>Mode Size : 0.2773(μm)<br>S.P. Area : 2.1008E+5(cm²/cm³)<br>Std.Dev. : 1.2818(μm)<br>Span : 0.8184<br>Diameter on Cumulative % : (1)10.00(%)- 0.2018(μm)<br>: (2)25.00(%)- 0.2372(μm)<br>: (3)50.00(%)- 0.2831(μm)<br>: (4)90.00(%)- 0.4335(μm)<br>: (5)95.00(%)- 4.0800(μm)<br>: (6)99.00(%)- 6.7452(μm)<br>: (7)99.90(%)- 9.2783(μm)</td></tr>
<tr><td>Genivida<br>(pre-grind)</td><td>Mean Size : 0.33229(μm)<br>Median Size : 0.22974(μm)<br>Mode Size : 0.2125(μm)<br>S.P. Area : 2.8129E+5(cm²/cm³)<br>Std.Dev. : 0.3361(μm)<br>Span : OFF<br>Diameter on Cumulative % : (1)10.00(%)- 0.1279(μm)<br>: (2)50.00(%)- 0.2297(μm)<br>: (3)90.00(%)- 0.6389(μm)<br>: (4)97.00(%)- 1.3898(μm)<br>: (5)99.00(%)- 1.7878(μm)<br>: (6)99.90(%)- 2.3748(μm)</td><td>Mean Size : 0.64002(μm)<br>Median Size : 0.27697(μm)<br>Mode Size : 0.2756(μm)<br>S.P. Area : 2.1409E+5(cm²/cm³)<br>Std.Dev. : 1.4022(μm)<br>Span : 0.8059<br>Diameter on Cumulative % : (1)10.00(%)- 0.1993(μm)<br>: (2)25.00(%)- 0.2331(μm)<br>: (3)50.00(%)- 0.2770(μm)<br>: (4)90.00(%)- 0.4225(μm)<br>: (5)95.00(%)- 4.4886(μm)<br>: (6)99.00(%)- 7.2623(μm)<br>: (7)99.90(%)- 10.1204(μm)</td></tr>
<tr><td>Genivida<br>(NO pre-grind)</td><td>Mean Size : 0.43150(μm)<br>Median Size : 0.24715(μm)<br>Mode Size : 0.2404(μm)<br>S.P. Area : 2.6019E+5(cm²/cm³)<br>Std.Dev. : 0.5135(μm)<br>Span : OFF<br>Diameter on Cumulative % : (1)10.00(%)- 0.1317(μm)<br>: (2)50.00(%)- 0.2471(μm)<br>: (3)90.00(%)- 1.1237(μm)<br>: (4)97.00(%)- 1.9698(μm)<br>: (5)99.00(%)- 2.5530(μm)<br>: (6)99.90(%)- 3.4743(μm)</td><td>Mean Size : 0.43005(μm)<br>Median Size : 0.28793(μm)<br>Mode Size : 0.2790(μm)<br>S.P. Area : 2.1057E+5(cm²/cm³)<br>Std.Dev. : 0.7244(μm)<br>Span : 0.7588<br>Diameter on Cumulative % : (1)10.00(%)- 0.2046(μm)<br>: (2)25.00(%)- 0.2410(μm)<br>: (3)50.00(%)- 0.2879(μm)<br>: (4)90.00(%)- 0.4231(μm)<br>: (5)95.00(%)- 0.5101(μm)<br>: (6)99.00(%)- 4.5476(μm)<br>: (7)99.90(%)- 6.1379(μm)</td></tr>
</table>

*FIG. 4*

SUSPENSION COMPOSITIONS OF PHYSIOLOGICALLY ACTIVE PHENOLIC COMPOUNDS AND METHODS OF MAKING AND USING THE SAME

TECHNICAL FIELD

The present disclosure relates to compositions including physiologically active phenolic compounds and methods for producing and utilizing such compositions. In certain embodiments, the compositions described herein comprise a nanoparticulate phenolic compound dispersed in an edible lipid, and in further embodiments, methods of making and using such compositions are provided.

BACKGROUND

There are a variety of physiologically active phenolic substances, including naturally-occurring phenolic compounds, that have been shown to exhibit favorable medicinal or nutritional properties. However, for a variety of reasons, it is often difficult to provide these phenolic compounds in a composition that is readily ingested and suited for delivering the compounds to subjects in sufficient amounts to achieve a desired nutritional or therapeutic effect.

Many phenolic substances are not readily bioavailable. As a result, in order to achieve any benefit from consumption or administration of the phenolic substance, a subject must consume or be administered large quantities of the phenolic compound. In addition, oral delivery of many desirable phenolic compounds has proven difficult or unpalatable to subjects, which can lead to a perceived requirement for parenteral routes of administration and/or the formulation of relatively complex, multi-component, pharmaceutical grade compositions designed to increase the targeted compound's bioavailability.

DESCRIPTION OF THE FIGURES

FIG. 1 provides the particle size distribution of Genivida™ (food grade genistein) upon receipt from a commercial supplier. FIG. 2 provides the particle size distribution of Bonistein® (pharmaceutical grade genistein) upon receipt from a commercial supplier.

FIG. 4 provides particle size distribution data for an exemplary physiologically active phenolic compound (genistein) prepared according to the present description and included within a composition as described herein. The genistein was sourced in two different grades, a pharmaceutical grade material (Bonistein®) and a food grade material (Genivida™). FIG. 4 provides initial particle size distribution data for the genistein materials prepared according to the methods described herein and included in a composition according to the present description ("Initial Measurement"). FIG. 4 also provides particle size distribution data for the same genistein materials after storage for three months ("3-Month Measurement") at ambient temperature.

DETAILED DESCRIPTION OF PREFERRED EMBODIMENTS

Figure 1:
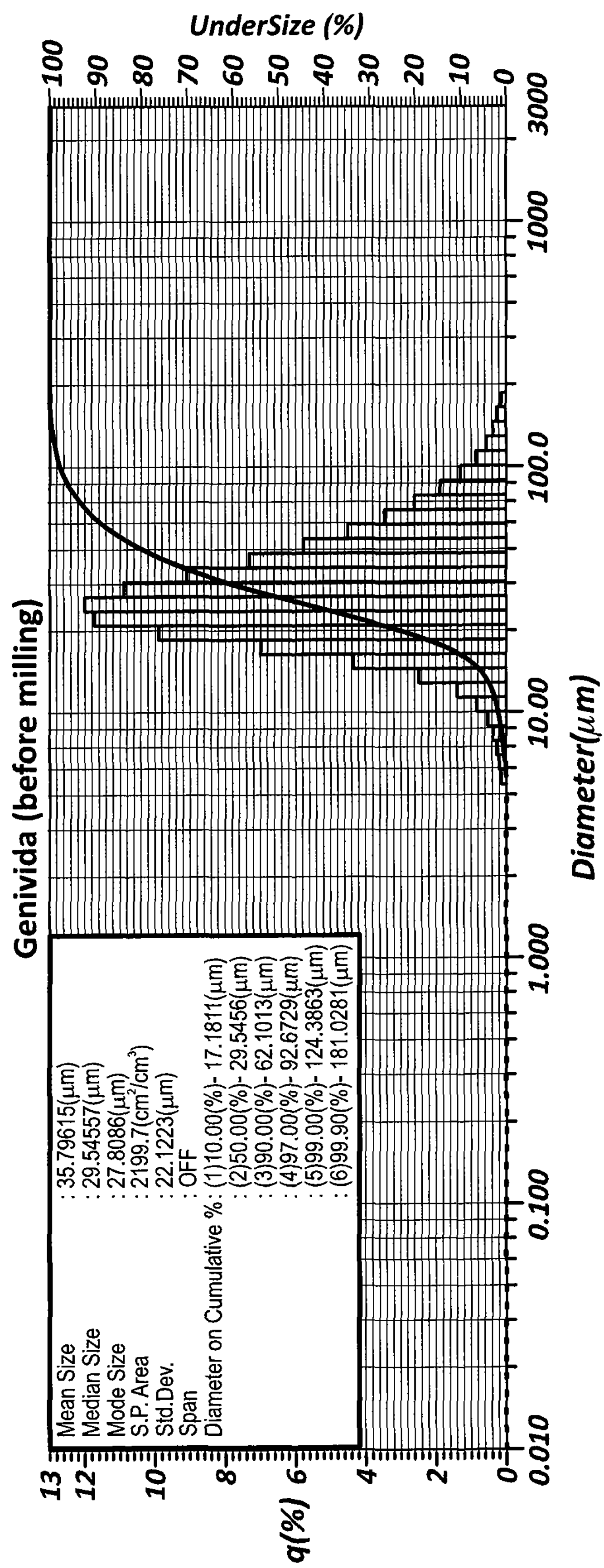
FIGS. 1 and 2 show the particle size distribution of two different grades of an exemplary physiologically active phenolic compound prior to preparation according to the methods described herein or inclusion in a composition according to the present description.

Compositions of physiologically active phenolic compounds are described herein. In certain embodiments, the compositions described herein are suitable for administration to or consumption by a subject as a pharmaceutical formulation, a medical food, or a dietary supplement. In particular embodiments, the compositions described herein include a phenolic compound provided as a nanoparticulate material suspended within an edible lipid. Providing the phenolic compound as nanoparticulate material serves to increase the bioavailability of the phenolic compound and may additionally facilitate administration or consumption of the phenolic compound at amounts sufficient to achieve a desired nutritional or therapeutic benefit.

Compositions prepared according to the present description have been shown to exhibit desirable physical stability characteristics. Often, where active compounds are provided as a nanoparticulate material, particle agglomeration over time causes a significant shift in the particle size distribution (PSD) of the active material, resulting in a loss of the advantages sought by providing the active as a nano-sized material in the first place. Embodiments of the compositions described herein serve to preserve the PSD of the phenolic compound included therein over time so that, even after months of storage, the PSD of the phenolic compound is maintained as a nanoparticulate material.

Methods for preparing the compositions described herein are also provided. In general, a physiologically active phenolic compound is provided as a nanoparticulate material and then dispersed within an edible lipid, resulting in a suspension suitable for administration to or consumption by a subject. Any suitable size reduction process may be utilized to reduce the phenolic compound to an active material exhibiting a desired, nano-sized PSD. In certain embodiments, the nanoparticulate phenolic compound material may be provided by a nano-milling procedure. The term "active material," as it is used in the present disclosure, refers to an amount of one or more physiologically active phenolic compound(s).

Nano-mills typically include a milling media (e.g., balls, beads, pellets, satellites, crystalline media, etc.) into which the active material to be size-reduced is introduced. Once the active material is introduced into the milling media, the milling media is agitated and the active material is subjected to grinding and shearing forces that reduce the material's PSD. In order to facilitate milling, the active material to be size-reduced can be provided in a liquid vehicle or a liquid vehicle may be introduced into the milling media. In specific embodiments of the methods described herein, the vehicle used in nano-milling the active material may be an edible lipid suitable for use in a composition according to the present description.

The compositions described herein are suitable for consumption by or administration to human and/or animal subjects. A composition according to the present disclosure may be prepared as a food-grade composition. Alternatively, a composition as described herein may be prepared as pharmaceutical-grade composition. In certain embodiments, the compositions described herein may be prepared for direct administration or consumption. In other embodiments, the compositions described herein may be prepared for combination with one or more other constituents prior to administration or consumption.

I. Definitions

As used herein and in the appended claims, the singular forms "a," "an," and "the" include plural reference unless the context clearly dictates otherwise.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "nanoparticulate" refers to material exhibiting a volume diameter, as measured using laser light diffraction, wherein the D (0.50) of the material is 0.5 μm or less. In certain embodiments, the term "nanoparticulate" refers to material exhibiting a volume diameter, as measured using laser light diffraction, wherein the D (0.50) of the material is 0.5 μm or less and the D (0.90) is 2 μm or less. Particle size analysis using laser light diffraction is a technique based on light being scattered through various angles which are directly related to the size of the particles. By measuring the angles of light scattered by the particles being analyzed and the intensity of this scattered light, a particle size distribution can be calculated. Techniques for use in analyzing particle size in the context of the present disclosure can be referred to as static light scattering, Rayleigh light scattering, low angle light scattering (LALS), multiple angle light scattering (MALS) Fraunhofer diffraction, or Mie Scattering. Measurement of particle size distributions using Mie Scattering allows for the determination of particle size distributions through the direction measurement of mass.

Two theoretical applications to the analysis of particle size by laser light diffraction are based on assumptions about the properties of the particles. Fraunhofer theory considers the following: particles are spherical, non-porous and opaque; particle diameters are greater than the wavelength of the laser light used in the analysis; and particles are distant enough from each other not to interfere in the diffraction of light, exhibit random motion, and diffract light with the same efficiency regardless of size and shape. Mie theory considers the differences in refractive index between the particles and the suspending medium, which allows the measurement technique to account for particles in the size range below the wavelength of the laser light used in the analysis. The relative amounts of different size particles are determined by measuring the intensity of light scattered at different angles. As the particles get close to or smaller than the wavelength of light, more of the light intensity is scattered to higher angles and back-scattered. Mie Scattering Theory accounts for this different behavior. In order to make particle size measurements, the light intensity pattern is measured over the full angular range. When the particle size is larger than the wavelength of the incident light, the Mie equation reduces to the Fraunhofer equation. An array of detectors, including high-angle and back-scatter detectors, and multiple light sources of different wavelengths are typically employed to allow measurement of the full size range in one analysis. Equipment suited for use in analyzing particle size by laser light diffraction is commercially available and manufactured, for example, by Horiba Instruments, Irvine, Calif.

In the context of the present description, the particle size distribution of a given material is provided in volume diameter as measured in accordance with USP 429 using a laser diffraction particle size analyzer operating in the Mie Scattering Theory diffraction mode and equipped with a suspension dispersion sample chamber (e.g., as available from Horiba Instruments, Irvine, Calif., USA). For purposes of the present description, volume diameter is given as a particle size distribution defined by one or more of D (0.10), D (0.50) and D (0.90). When referred to herein, the term D (0.10) indicates the volume frequency distribution of particles for which 10% of the sample is below the referenced size, the term D (0.50) indicates the volume frequency distribution of particles for which 50% of the sample is below the referenced size, and the term D (0.90) indicates the volume frequency distribution of particles for which 90% of the sample is below the referenced size. In addition to measurement of the particle size distribution via laser diffraction, the results from such particle size analysis and/or the morphology of the particles may be confirmed using known electron microscopy techniques.

A "subject" for purposes of this disclosure is an animal to which a composition as described herein can be administered in order to achieve a targeted benefit. In certain embodiments, the subject is a human being.

II. Compositions of Physiologically Active Phenolic Compounds

The compositions described herein include one or more physiologically active phenolic compound. The phenolic compound may be a non-naturally occurring or a naturally occurring compound. In addition, the phenolic compound may be chemically synthesized (even if also produced by natural sources) or isolated, purified, or derived from natural sources. In particular embodiments, the phenolic compound is a naturally occurring compound found in or derived from one or more species or varieties of plant. Examples of such compounds suitable for use in the compositions described herein include, but are not limited to, compounds selected from isoflavones, curcuminoids, flavonols, and stilbenoids.

Curcuminoids are natural phenols found, for example, in turmeric. Curcuminoids include curcumin, desmethoxycurcumin, and bis-desmethoxycurcumin. Curcumin can exist in several tautomeric forms, including a 1,3-diketo form and two equivalent enol forms. Curcuminoids generally exhibit poor water solubility and poor bioavailability. The chemical name for curcumin is (1E,6E)-1,7-bis(4-hydroxy-3-methoxyphenyl)-1,6-heptadiene-3,5-dione (IUPAC). The chemical name for desmethoxycurcumin is (1E,6E)-1,6-Heptadiene-3,5-dione, 1-(4-hydroxy-3-methoxyphenyl)-7-(4-hydroxyphenyl) (IUPAC). The chemical name for bis-desmethoxycurcumin is (1E,6E)-1,7-bis(4-hydroxyphenyl) hepta-1,6-diene-3,5-dione (IUPAC). Curcuminoids are commercially available and can be isolated from plant material or manufactured in purified form using known chemical syntheses.

Isoflavones include a variety of naturally occurring compounds and belong to a class of organic compounds related to isoflavonoids. Many isoflavones act as phytoestrogens in mammals, and some are termed antioxidants because of their ability to trap singlet oxygen. Isoflavones are produced almost exclusively by the members of the Fabaceae family (i.e., the Leguminosae or bean family). Soybeans are the most common source of isoflavones in human food, and the major isoflavones in soybean are genistein and daidzein. In general, isoflavones also exhibit poor water solubility and bioavailability. Genistein is commercially available and may be obtained in synthetic, purified form. Synthetic genistein is available, for example, as BONISTEIN from DSM Nutritional Products (DSM Nutritional Products, Inc. Parsippany, N.J.). Genistein's chemical name is 5,7-dihydroxy-3-(4-hydroxyphenyl)-chromen-4-one (IUPAC). Daidzein's chemical name is 7-hydroxy-3-(4-hydroxyphenyl) chromen-4-one (IUPAC). Like genistein, daidzein is commercially available and can be extracted or isolated from plant material or manufactured in purified form using known chemical syntheses.

Flavanols that may be utilized in compositions according to the present description include catechins. As used herein, the term "catechin" refers to a family of compounds as well as the compound itself. Catechin has the chemical name (2R, 3S)-2-(3,4-dihydroxyphenyl)-3,4-dihydro-2H-chromene-3, 5,7-triol (IUPAC). The family of catechin compounds includes, for example, epicatechin, and epigallocatechin gallate (EGCG), which may also be used in compositions, described herein. As used herein, "epicatechin" refers to one or both of two isomers of catechin in the cis configuration, and when used herein as a compound name, the term "catechin" refers to one or both of two isomers of catechin in the trans configuration. The chemical name for EGCG is [(2R,3R)-5, 7-dihydroxy-2-(3,4,5-trihydroxyphenyl)chroman-3-yl]3,4, 5-trihydroxybenzoate (IUPAC). Catechins are commercially available and can be found in and isolated from, for example, green tea, cocoa beans, the kola nut, raw apples, apricots, nectarines, pears and plums, blackberries, red raspberries, cranberries, cherries, broad beans. Catechins can also be manufactured in purified form using known chemical syntheses.

Stilbenoids are naturally occurring phenols produced by several different plants. A stilbenoid of particular interest in the context of the compositions described herein is resveratrol. The chemical name for resveratrol is 5-[(E)-2-(4-hydroxyphenyl)ethenyl]benzene-1,3-diol (IUPAC). Like other stilbenoids, resveratrol produced naturally by several different species of plants, and it is often extracted for commercial purposes from the roots of the Japanese Knotweed. Like the other phenol compounds specifically described herein, resveratrol is commercially available and can be isolated from naturally occurring plant material or manufactured in purified form using known chemical syntheses.

The composition described herein may include one or more phenolic compounds as described herein. For example, in particular embodiments, the compositions include a phenolic compound selected from curcumin, desmethoxycurcumin, bis-desmethoxycurcumin, genistein, daidzein, catechin, epicatechin, EGCG, resveratrol, and combinations of two of more of such compounds. In each embodiment, one or more phenolic compound included in the composition is provided as a nanoparticulate material. In specific embodiments, the compositions disclosed herein may include one or more phenolic compounds provided as nanoparticulate material exhibiting a D (0.50) of 0.4 μm or less. In certain such embodiments, the compositions disclosed herein may include one or more phenolic compounds provided as nanoparticulate material exhibiting a D (0.50) selected from a D (0.50) of 0.35 μm or less, a D (0.50) of 0.30 μm or less, a D (0.50) of 0.25 μm or less, and a D (0.50) of 0.20 μm or less. In addition to being characterized by a D (0.50) as detailed herein, the nanoparticulate active material may exhibit a D (0.90) of 2.0 μm or less. In particular embodiments, the nanoparticulate active material exhibits a D (0.50) as detailed herein and a D (0.90) selected from a D (0.90) of 1.5 μm or less, a D (0.90) of 1.0 μm or less, and a D (0.90) of 0.5 μm or less.

Nanoparticulate active material suitable for use in the compositions disclosed herein may be prepared according to known methods for producing materials exhibiting a sub-micron PSD. In one embodiment, naturally derived or synthetically manufactured phenolic compound material may be nanomilled according to milling techniques known in the art. Nanomilling may include wet bead milling utilizing an agitator bead mill in a grinding container for continuous dispersion and fine wet grinding. Alternatively, the necessary energy for dispersion and grinding of a material within the milling media of a nanomill may be transmitted to the grinding media through agitator discs mounted on an agitator shaft. Several different nanomills and milling techniques are commercially accessible and offered from, for example, CB Mills, of Gurnee, Ill., and NETZSCH Premier Technologies, LLC of Exton, Pa.

Though nanomilling is generally referenced herein as a means for producing nanoparticulate active material suitable for use in the compositions described herein, the nanoparticulate active material can be produced by other suitable techniques as well. For example, the desired phenolic compound may be provided as a nanoparticulate material through one or more known wet milling techniques, super-critical or compressed fluid techniques, hot or high-pressure homogenization, emulsification techniques, evaporative precipitation, antisolvent precipitation, microprecipitation, cryogenic techniques, complexation techniques, ultrasonication techniques, solid dispersion techniques, or spray drying and lyophilization techniques.

The active material included in the compositions described herein is dispersed within an edible lipid to form a nanoparticulate suspension of the phenolic compound. The term "edible lipid" refers to naturally occurring and synthetic lipids, fats, and oils suitable for consumption by or administration to a subject. In certain embodiments, the edible lipid may be an edible glyceride selected from glycerides having a chain length ranging from one carbon acetate to 22 carbons. Where an edible glyceride is used as the edible lipid, the fatty acid chain of the edible glyceride may be saturated or exhibit varying degrees of unsaturation. In particular embodiments where the edible glyceride includes an unsaturated fatty acid chain the degree of unsaturation may range from one double bond (e.g., oleic acid) up to six double bonds (e.g., docosahexaenoic acid). Further, the fatty acid residues of edible glycerides suitable for use in the compositions described herein may form an ester linkage on one (mono-glyceride), two (di-glyceride), or all three glycerol hydroxyl groups (triglyceride). Any hydroxyl groups not esterified may be free hydroxyl groups or chemically linked to, for example, phosphate, inositols, choline, serine, or ethanol amine, such as found in lecithin.

The edible lipid used in the compositions described herein may also be selected from edible lipids, oils, and fats from plant and animal sources. Plant oils that may be suitable for use in the compositions described herein include, for example, olive, corn, soy, marine, coconut, palm, palm kernel, cotton seed, peanut, safflower, sesame, sunflower, almond, cashew, macadamia, pecan, pine nut, walnut, lemon, orange, flax seed, and borage oils. Where the edible lipid is a plant oil or is derived from one of the plant oils detailed herein, the edible lipid may also be selected from cocoa butter or an inter-esterified plant oil, such as medium-chain triglycerides formed from one or more of the plant oils detailed herein. Animal oils and fats that may be suitable for use in the compositions described herein include fish oils and dairy derived fats, such as butter.

The nanoparticulate active material can be suspended within the edible lipid at various concentrations. The compositions described herein can be prepared with high concentrations of the nanoparticulate material, and in certain embodiments, the nanoparticulate material is suspended in the edible lipid at a concentration of 200 mg/ml or higher. For example, compositions according to the present description may include the nanoparticulate material suspended within the edible lipid at a concentration selected from 200 mg/ml or higher, 250 mg/ml or higher, 300 mg/ml or higher, 350 mg/ml or higher, 400 mg/ml or higher, 450 mg/ml or higher, and 500 mg/ml or higher.

Compositions according to the present description may additionally include edible colorants, flavorants, and dispersants. A wide variety of colorants and flavorants suitable for human and animal consumption are well known and readily commercially available. Where included in the compositions described, a dispersant, which may be an edible emulsifier, may serve to help maintain or improve particle size stability within the suspension and/or bioavailability of the phenolic compound(s) dispersed therein. The edible dispersant may be selected from, for example, lecithin, and sorbitan fatty acid esters, such as polysorbate 80, steroyl-2-lactate, polyoxyethylene esters, sucrose esters of fatty acids, polyglycerol esters, fatty acid esters of propyleneglycol, and glycerol fatty acid esters. Where included, a dispersant may be provided in a relative amount selected from about 0.01% to about 5% (w/v).

The compositions described herein can be prepared for use in different contexts. For example, the compositions may be prepared for oral consumption as a dietary supplement, a medical food, or even as a pharmaceutical formulation. Where prepared as a dietary supplement or a medical food, the phenolic compound(s), edible lipid, and, where included, any colorant, flavorant, or dispersant included in the composition can be prepared and provided as a food-grade material such that the resulting composition is a food-grade composition suitable for use as a medical food or dietary supplement. If desired, in other embodiments, the compositions described herein can be prepared for use as a pharmaceutical composition. In such embodiments, each of the components must be prepared as pharmaceutical grade materials such that a pharmaceutical grade composition is produced.

The compositions described herein may be prepared in any suitable manner and using any suitable devices. Moreover, compositions according to the present description can be prepared for oral consumption or oral or parenteral administration via a variety of delivery devices or mechanisms. For example, the suspension compositions described herein can be prepared for delivery from any desired metering device, including a syringe, measuring spoon, cup, or vial, and where desired to ease administration or delivery, the compositions according to the present description can be metered in pre-measured amounts into syringes, sachets, or capsules, such as gelatin or soft capsules, suited for delivery of suspension or dispersion compositions. Particularly when used as a medical food or dietary supplement, the compositions described herein may also be prepared for distribution over or within other foods, liquids, or dry goods for consumption by the intended subject.

III. Methods

Methods for preparing the compositions described herein are provided. In certain embodiments, methods for preparing a composition as described herein include providing a phenolic compound as a nanoparticulate material, providing an edible lipid as described herein, and mixing the nanoparticulate phenolic compound material with the edible lipid to disperse the nanoparticulate phenolic compound material and form a suspension composition. In such embodiments, one or more additional materials may also be provided for inclusion in the composition. For example, one or more dispersants may be provided and combined with the nanoparticulate phenolic compound material and the edible lipid. Where one or more dispersants are included, the dispersant may be combined with the edible lipid prior to the introduction of the nanoparticulate phenolic compound. Alternatively, one or more dispersants may be combined with the nanoparticulate phenolic compound material prior to combination of the dispersant and phenolic compound with the edible lipid. Even further, one or more dispersants may be combined with the edible lipid and nanoparticulate phenolic compound after the nanoparticulate phenolic compound has been dispersed within the edible lipid.

In yet further embodiments, the compositions described herein can be prepared by forming the nanoparticulate active material in the presence of the edible lipid, where the edible lipid forms part of the medium within which the size comminution of the phenolic compound takes place. In certain such embodiments, the active material is processed to a desired nanoparticulate PSD using a nanomill, wherein the active material is combined with the edible lipid prior to introduction into the nanomill. In other such embodiments, the active material and edible lipid are introduced into the nanomill separately (e.g., the phenolic compound material and edible lipid may be introduced to the milling media in separate process steps, the edible lipid may be combined with the milling media prior to introduction of the active material, or the active material may be combined with the milling media prior to introduction of the edible lipid).

In specific embodiments where the active material and edible lipid are combined in a nanomill, the active material and edible lipid are fed into the nanomill and milled in a manner that results in a composition characterized by nanoparticulate active material suspended within the edible lipid. In one such embodiment, a suspension of active material and edible lipid may be fed continuously through the nanomill until a suspension composition containing nanoparticulate active material of a desired PSD is reached. For example, the active material may be nanomilled by recirculating a volume of the active material suspended within the edible lipid, followed by one or more single passes through the nanomill to reach a composition that includes a phenolic compound material exhibiting the desired PSD. The particle size of the active material suspended within a composition as described herein can be controlled by adjusting the parameters of the nanomill and the grinding conditions. For example, the particle size produced by nanomilling the active material or a combination of active material and edible lipid may be controlled by the size of the milling media, load/suspension weight ratio of the milling media, suspension composition (e.g., the amount of active material relative to the amount of edible lipid), agitation rate, and milling time.

Depending on the nature of the active material, one or more pre-milling steps may also be utilized prior to a final nanomilling process. Pre-milling of the active material may be carried out using any suitable method and system for size comminution of the active material. Pre-milling may be particularly helpful where the active material, as supplied, exhibits a relatively coarse PSD. By subjecting the active material to a pre-milling step, the PSD of the active material can be reduced to better approximate the targeted nanoparticulate PSD and, thereby, reduce the process time required in the final milling process. Such an approach may be particularly advantageous where the active material is to be milled in an edible lipid, as the edible lipid and/or active material may be adversely affected by prolonged exposure to the heat, shear, and grinding forces that could be required to reduce the PSD of a coarse active material to a suitable nanoparticulate range. A premilling step may also allow sourcing and use of active material that exhibits relatively coarse initial particle size characteristics, which, in turn, may lead to cost savings in the materials used for preparation of compositions according to the present description.

Methods for administering the physiologically active phenolic compounds included in the compositions described herein are also provided. The active materials described herein have several potential nutritional and therapeutic benefits, with many being recognized as powerful antioxidants and considered to confer nutritional and therapeutic benefits to subjects suffering from or at risk of conditions ranging from various forms of inflammation to certain forms of cancer. Additionally, physiologically active phenolic compounds disclosed herein have been associated with potential cardioprotective and neuroprotective effects, particularly when consumed over time. Even further, physiologically active phenolic compounds specified herein have been used to ameliorate symptoms associated with changes in hormone levels or production in subjects.

The compositions described herein will typically be consumed or administered orally, and in such embodiments, the amount and frequency with which the composition is consumed by a subject may depend on the desired nutritional or therapeutic benefit to be achieved, the nature of the phenolic compound(s) included in the composition, and the physical characteristics of the subject (e.g., age, weight, gender). The compositions described herein may be administered or consumed, for example, as a single dose, a regular daily dose, a two-times daily dose, a three-times daily dose, or according to another desired schedule. Moreover, in specific embodiments, a composition as described herein may be administered to or consumed by a subject in an amount sufficient to deliver a dose of a phenolic compound contained therein that ranges from about 50 mg/day to about 10,000 mg/day. In certain such embodiments, the composition is delivered to or consumed by the subject in an amount sufficient to deliver a dose of phenolic compound selected from about 50 mg/day to about 9,000 mg/day, about 50 mg/day to about 8,000 mg/day, about 50 mg/day to about 2,000 mg/day, about 100 mg/day to about 9,000 mg/day, about 100 mg/day to about 5,000 mg/day, about 100 mg/day to about 4,000 mg/day, about 100 mg/day to about 2,000 mg/day, and about 100 mg/day to about 1,000 mg/day.

EXAMPLES

Example 1

Preparation of Nano Particulate Compositions of Genistein

Figure 2:
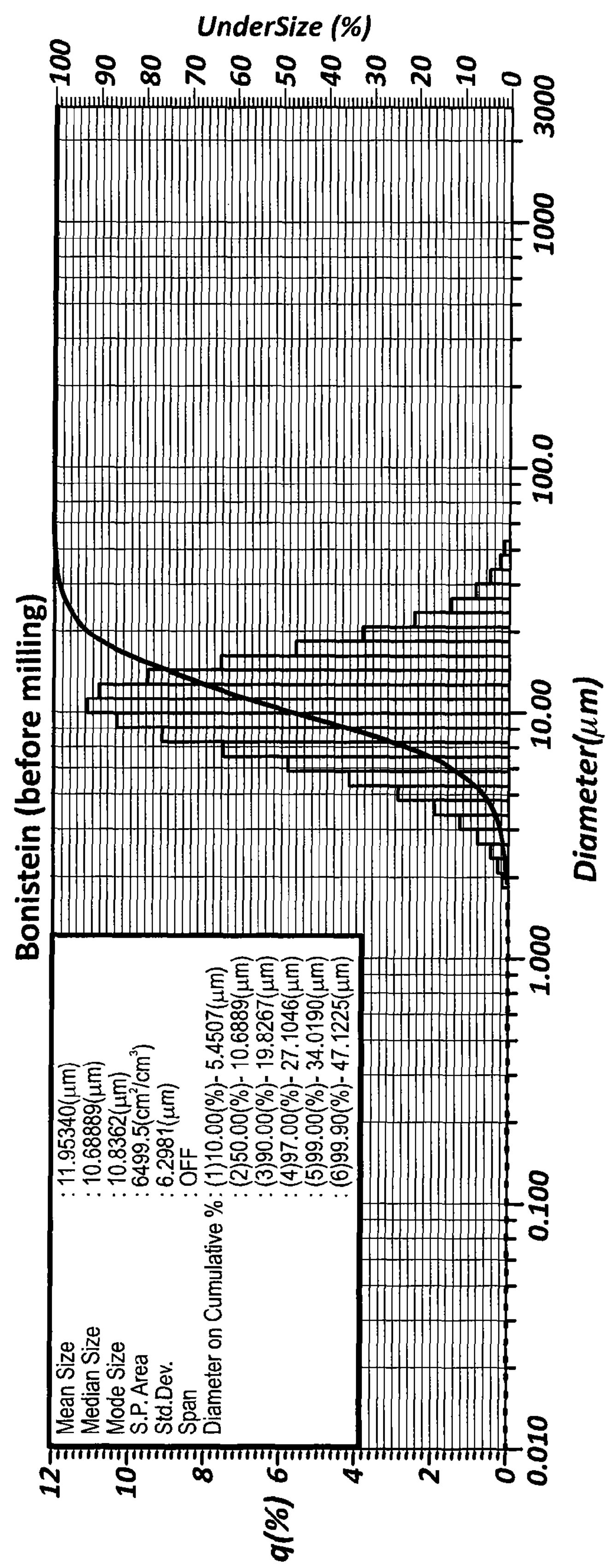

Materials:

Genivida™, a food grade genistein, and Bonistein®, a pharmaceutical grade genistein, were obtained from a commercial supplier (DSM, http://www.dsm.com/corporate/home.html) and subjected to particle size analysis. As provided, the Genivida™ material exhibited a D(0.50) particle size 29.5 μm, and the Bonistein® material exhibited a D(0.50) particle size 10.7 μm. FIG. 1 and FIG. 2 illustrate the PSD of the Genivida™ and Bonistein® materials as supplied from DSM.

A food grade, 100% olive oil was obtained for use as an edible lipid. The olive oil was purchased from a supermarket and was a generic Mediterranean olive oil blend containing olive oils from Italy, Spain, Tunisia, Turkey, and Morocco.

Methods:

The Genivida™ and Bonistein® materials were dispersed within the olive oil to provide a suspension composition that included 25% (w/v) genistein. Several samples (≈200 ml per sample) of the 25% w/v genistein/olive oil suspension were divided and milled using a, MiniCer® nanomill from Netzsch. The samples containing Bonistein® were milled for 60 minutes in a 0.3 mm YTZ media (yttria stabilized zirconium oxide ($ZrO_2$) beads). Samples containing Genivida™ were milled for 60 minutes in a 0.5 mm YTZ media.

A selection of the samples containing Genivida™ were subjected to a pre-milling process (referred to or labeled as "pre-grind" samples). The pre-milling process also utilized a MiniCer® nanomill from Netzsch with YTZ milling media. However, the milling media utilized in the pre-milling step was 1.25 mm YTZ media. Pre-milling was carried out for 20 minutes, with the purpose of reducing the D(0.50) particle size of the Genivida™ to below 10 μm. After pre-milling, those samples subjected to the pre-milling procedure were milled in a MiniCer® nanomill for 60 minutes in a 0.3 mm YTZ media.

After the milling steps, particle size analysis was completed for each sample. Milling of the genistein compositions resulted in a size comminution of the Bonistein® and Genivida™ materials, with each sample exhibiting a nanoparticulate PSD (see, FIG. 4). An amount of each nanosuspension composition was aliquoted into 3.7 cc glass vials, which were then stored at ambient temperature.

At approximately two months, samples were taken from each vial and subjected to laser diffraction particle size analysis and TEM analysis. Particle size analysis and distribution obtained by TEM analysis was consistent with that obtained by laser diffraction analysis, and showed that the genistein material suspended within the samples maintained a nanoparticulate PSD.

Figure 3A:
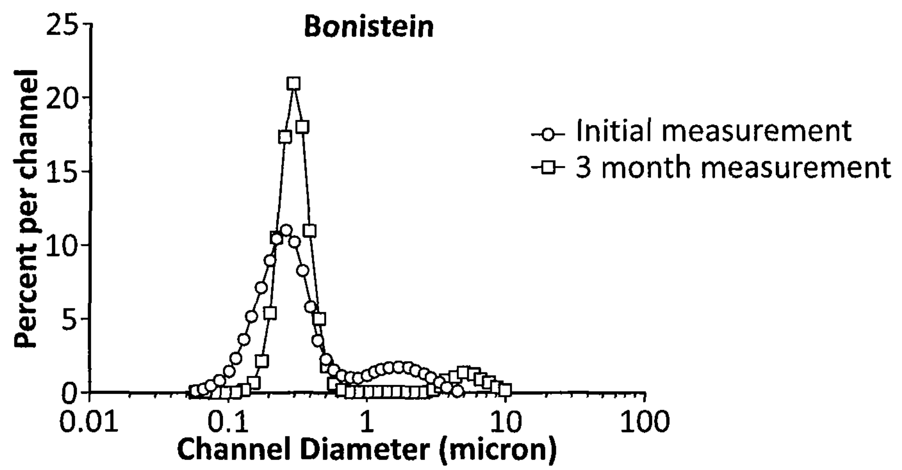
FIGS. 3A-3C show the initial and 3-month particle size distributions for two different grades of an exemplary nanoparticulate, physiologically active, phenolic compound material (nanoparticulate genistein) prepared according to the methods described herein and included within compositions according to the present description.
Figure 3B:
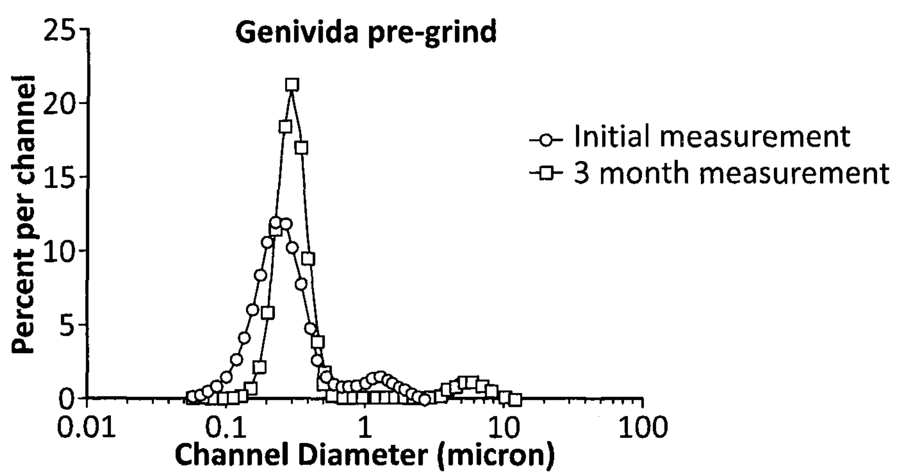
Figure 3C:
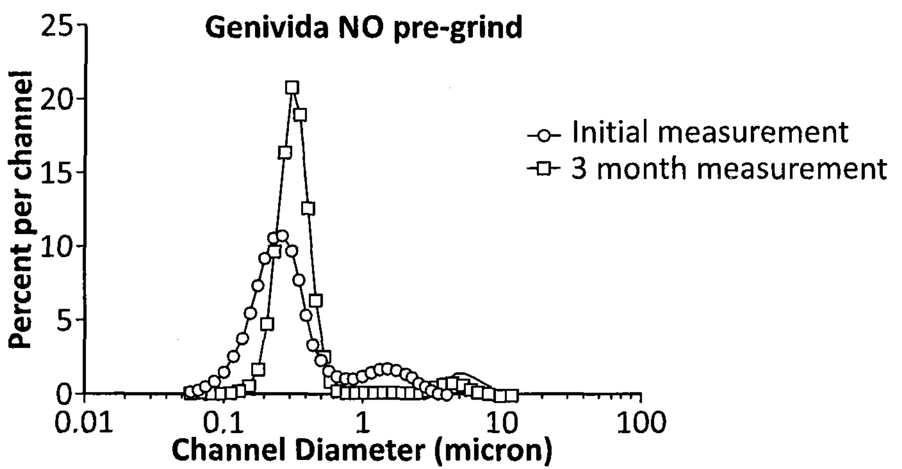

At the 3-month time point, a sample of each nanosuspension was taken from each vial and again subjected to laser diffraction particle size analysis and TEM analysis. Even after three months, the genistein material suspended in the olive oil remained nano-sized, with the D(0.50) at 3 months in all cases being <300 nm (see, FIGS. 3A-3C).

For each of the samples at each time point, particle size analysis conducted by laser diffraction was carried out using a LA-950 particle size analyzer from Horiba Scientific, Edison, N.J.

The invention claimed is:

1. A composition suitable for consumption by a subject, the composition comprising:

an edible lipid; and an active material suspended within the edible lipid forming a nanoparticulate suspension, wherein the active material comprises a physiologically active phenolic compound and exhibits a particle size distribution characterized by a D (0.50) of 0.5 μm or less.

2. The composition according to claim 1, wherein the active material exhibits a particle size distribution characterized by a D (0.50) selected from a D (0.50) of 0.4 μm or less, a D (0.50) of 0.35 μm or less, a D (0.50) of 0.30 μm or less, a D (0.50) of 0.25 μm or less, and a D (0.50) of 0.20 μm or less.

3. The composition according to claim 2, wherein the active material exhibits a particle size distribution characterized by a D(0.50) of 0.3 μm or less.

4. The composition according to claim 2, wherein the active material exhibits a particle size distribution characterized by a D (0.90) of 2.0 μm or less.

5. The composition according to claim 4, wherein the active material exhibits a particle size distribution characterized by a D (0.90) selected from a D (0.90) of 1.5 μm or less, a D (0.90) of 1.0 μm or less, and a D (0.90) of 0.5 μm or less.

6. The composition according to claim 2, wherein the physiologically active phenolic compound is selected from the group consisting of isoflavones, curcuminoids, flavonols, stilbenoids, and combinations thereof.

7. The composition according to claim 6, wherein the physiologically active phenolic compound is selected from the group consisting of curcumin, desmethoxycurcumin, bisdesmethoxycurcumin, genistein, daidzein, catechin, epicatechin, EGCG, resveratrol, and combinations of two of more of such compounds.

8. The composition according to claim 6, wherein the physiologically active phenolic compound is genistein.

9. The composition according to claim 6, further comprising a dispersant selected from the group consisting of lecithin, polysorbate 80, steroyl-2-lactate, polyoxyethylene esters, sucrose esters of fatty acids, polyglycerol esters, fatty acid esters of propylene glycol, and glycerol fatty acid esters.

10. The composition according to claim 6, wherein the edible lipid is an edible glyceride having a chain length ranging from one carbon acetate to 22 carbons, and wherein the edible glyceride is selected from the group consisting of mono-glycerides, di-glycerides, and triglycerides.

11. The composition according to claim 6, wherein the edible lipid is an edible plant oil or animal oil selected from the group consisting of olive, corn, soy, marine, coconut, palm, palm kernel, cotton seed, peanut, safflower, sesame, sunflower, almond, cashew, macadamia, pecan, pine nut, walnut, lemon, orange, flax seed, borage oils, fish oils, and dairy derived fats.

12. The composition according to claim 8, wherein the edible lipid comprises olive oil.

13. A method for preparing an edible suspension of a physiologically active phenolic compound, the method comprising:

providing an edible lipid;

providing an active material comprising a physiologically active phenolic compound; and milling the active material in the presence of the edible lipid to form a nanoparticulate suspension of the active material suspended within the edible lipid, wherein the active material in the nanoparticulate suspension exhibits a particle size distribution characterized by a D(0.50) of 0.5 μm or less, and wherein milling the active material in the presence of the edible lipid comprises nanomilling the active material in a milling media that comprises the edible lipid.

14. The method according to claim 13, wherein, prior to milling the active material in the presence of the edible lipid, the active material is suspended within the lipid and milling the active material in the presence of the edible lipid comprises introducing the combined active material and edible lipid into a nanomill and processing the combined active material and lipid within the nanomill until the active material exhibits a desired particle size distribution.

15. The method according to claim 13, wherein milling the active material in the presence of the edible lipid comprises milling the active material until the active material exhibits a particle size distribution characterized by a D (0.50) selected from a D (0.50) of 0.4 μm or less, a D (0.50) of 0.35 μm or less, a D (0.50) of 0.30 μm or less, a D (0.50) of 0.25 μm or less, and a D (0.50) of 0.20 μm or less.

16. The method according to claim 15, wherein milling the active material in the presence of the edible lipid comprises milling the active material until the active material exhibits a particle size distribution characterized by a D(0.50) of 0.3 μm or less.

17. The method according to claim 15, wherein milling the active material in the presence of the edible lipid comprises milling the active material until the active material exhibits a particle size distribution characterized by a D (0.90) of 2.0 μm or less.

18. The method according to claim 17, wherein milling the active material in the presence of the edible lipid comprises milling the active material until the active material exhibits a particle size distribution characterized by a D (0.90) selected from a D (0.90) of 1.5 μm or less, a D (0.90) of 1.0 μm or less, and a D (0.90) of 0.5 μm or less.

19. The method according to claim 15, wherein the physiologically active phenolic compound is selected from the group consisting of isoflavones, curcuminoids, flavonols, stilbenoids, and combinations thereof.

20. The method according to claim 19, wherein the physiologically active phenolic compound is selected from the group consisting of curcumin, desmethoxycurcumin, bisdesmethoxycurcumin, genistein, daidzein, catechin, epicatechin, EGCG, resveratrol, and combinations of two of more of such compounds.

21. The method according to claim 20, wherein the physiologically active phenolic compound is genistein.

22. The method according to claim 19, further comprising providing a dispersant, wherein the dispersant is blended with the edible lipid and the active material, and wherein the dispersant is selected from the group consisting of lecithin, polysorbate 80, steroyl-2-lactate, polyoxyethylene esters, sucrose esters of fatty acids, polyglycerol esters, fatty acid esters of propyleneglycol, and glycerol fatty acid esters.

23. The method according to claim 19, wherein the edible lipid is an edible glyceride having a chain length ranging from one carbon acetate to 22 carbons, and wherein the edible glyceride is selected from the group consisting of mono-glycerides, di-glycerides, and triglycerides.

24. The method according to claim 19, wherein the edible lipid is an edible plant oil or animal oil selected from the group consisting of olive, corn, soy, marine, coconut, palm, palm kernel, cotton seed, peanut, safflower, sesame, sunflower, almond, cashew, macadamia, pecan, pine nut, walnut, lemon, orange, flax seed, borage oils, fish oils, and dairy derived fats.

25. The composition according to claim 1, wherein the concentration of the active material in the nanoparticulate suspension is 200 mg/ml or higher.

26. The composition according to claim 25, wherein the concentration of the active material in the nanoparticulate suspension is selected from a concentration of 250 mg/ml or higher, a concentration of 300 mg/ml or higher, a concentration of 350 mg/ml or higher, a concentration of 400 mg/ml or higher, a concentration of 450 mg/ml or higher, and a concentration of 500 mg/ml or higher.

27. The method according to claim 13, wherein the concentration of the active material in the nanoparticulate suspension is 200 mg/ml or higher.

28. The method according to claim 27, wherein the concentration of the active material in the nanoparticulate suspension is selected from a concentration of 250 mg/ml or higher, a concentration of 300 mg/ml or higher, a concentration of 350 mg/ml or higher, a concentration of 400 mg/ml or higher, a concentration of 450 mg/ml or higher, and a concentration of 500 mg/ml or higher.

29. The method according to claim 19, wherein the concentration of the active material in the nanoparticulate suspension is 200 mg/ml or higher.

30. The method according to claim 29, wherein the concentration of the active material in the nanoparticulate suspension is selected from a concentration of 250 mg/ml or higher, a concentration of 300 mg/ml or higher, a concentration of 350 mg/ml or higher, a concentration of 400 mg/ml or higher, a concentration of 450 mg/ml or higher, and a concentration of 500 mg/ml or higher.

* * * * *